United States Patent [19]
Muderlak et al.

[11] Patent Number: 5,908,140
[45] Date of Patent: Jun. 1, 1999

[54] MATERIAL DISPENSING METHOD AND APPARATUS WITH STALL DETECT

[75] Inventors: Kenneth J. Muderlak, Shorewood, Wis.; Rocky Sheih, Hsin Chu, Taiwan

[73] Assignee: Technical Concepts, L.P., Mundelein, Ill.

[21] Appl. No.: 08/916,051

[22] Filed: Aug. 21, 1997

[51] Int. Cl.⁶ ............................................. B67B 7/00
[52] U.S. Cl. ................... 222/1; 222/63; 222/646; 222/333; 222/504
[58] Field of Search .................... 222/192, 644, 222/645, 646, 648, 649, 63, 1, 333, 504

[56] References Cited

U.S. PATENT DOCUMENTS

| | | |
|---|---|---|
| Re. 34,847 | 2/1995 | Muderlak et al. . |
| 3,891,909 | 6/1975 | Newson . |
| 4,063,664 | 12/1977 | Meetze . |
| 4,099,704 | 7/1978 | Okumura et al. . |
| 4,220,900 | 9/1980 | Mintz . |
| 4,350,265 | 9/1982 | Griffiths et al. . |
| 4,394,605 | 7/1983 | Terazawa . |
| 4,455,012 | 6/1984 | Gupta . |
| 4,544,893 | 10/1985 | Takahashi . |
| 4,709,196 | 11/1987 | Mizuta . |
| 4,795,883 | 1/1989 | Glucksman et al. . |
| 4,830,791 | 5/1989 | Muderlak . |
| 4,858,468 | 8/1989 | Tahara et al. . |
| 5,046,655 | 9/1991 | Kor et al. . |
| 5,064,120 | 11/1991 | Luttrell . |
| 5,111,477 | 5/1992 | Muderlak . |
| 5,130,659 | 7/1992 | Sloan . |
| 5,249,718 | 10/1993 | Muderlak . |
| 5,315,564 | 5/1994 | Upton . |
| 5,406,188 | 4/1995 | Myslinski et al. . |
| 5,449,117 | 9/1995 | Muderlak et al. . |
| 5,488,276 | 1/1996 | Nishibe . |

FOREIGN PATENT DOCUMENTS

| 0010391 | 4/1990 | European Pat. Off. . |
|---|---|---|

*Primary Examiner*—Gregory L Huson
*Attorney, Agent, or Firm*—Sonnenschein Nath & Rosenthal

[57] ABSTRACT

An apparatus for dispensing material from a container having a dispensing element includes a motor for repeatedly actuating the dispensing element to facilitate dispensing of the material from the container and a controller for activating the motor at predetermined time intervals. The apparatus includes a stall detection circuit coupled to the motor and to the controller to detect a stall condition of the motor, the stall detection circuit configured to issue a stall detection signal when the stall condition is detected. The controller deactivates the motor in response to receiving the stall detection signal.

24 Claims, 6 Drawing Sheets

MATERIAL DISPENSING METHOD AND APPARATUS WITH STALL DETECT

BACKGROUND OF THE INVENTION

The present invention relates generally to devices for repeatedly dispensing material and more specifically to an energy conserving dispensing device and method for dispensing material. In the past, various solid materials were utilized which sublimated, thereby dispersing a substitute odor for the odor found in public facilities. In order to enhance the dispersion of such sublimating materials, many suppliers developed powered fan devices which assisted in the dispersal of the sublimated material. Such devices are well known in the art. For example, the common assignee of the present invention owns U.S. Pat. No. 4,830,791 entitled Odor Control Device, issued May 16, 1989 which discloses a solid dispensing device. Also, odor control devices where a pressurized aerosol container is utilized are well known in the art. Aerosol-type dispensing devices typically include a battery powered motor that actuates the nozzle on the aerosol container on a periodic basis. Known devices have significant disadvantages. These devices do not inform the user of the amount of time or the number of days remaining until the container must be replaced or refilled. Additionally, such devices are not particularly energy efficient and if powered by batteries, require frequent servicing to replace the batteries.

It is also known to use liquid containers for dispensing odorizing liquid. Typically, a dispensing tube attached to the container directs a flow of liquid cleaning, disinfecting, or odorizing chemical (e.g. directly into a toilet bowl or the inside wall of a urinal). Such devices may also operate based on the flush action of a urinal or toilet and are referred to as in-line devices. One known device is a system for injecting metered amounts of chemicals into flush water as the flush water enters the toilet.

The above-described devices are usually battery powered to simplify installation. Because connection to a conventional AC outlet is not required for battery powered devices, installation is simplified and cost is reduced. When the batteries become depleted, the unit ceases to function. Accordingly, the batteries must be replaced periodically. Frequent replacement of the batteries is a significant disadvantage that becomes even more troublesome in devices that are not particularly energy efficient. Replacement of the batteries, if performed at unnecessarily frequent intervals, is an annoying task that increases maintenance costs and customer dissatisfaction. The problem of battery disposal also gives rise to environmental concerns. Customers are unwilling to perform frequent battery replacement and have been known to replace the entire device when battery replacement is required too frequently. Often, the device is replaced with an alternate model or a different manufacturer's device.

In any motorized device, a portion of the battery's energy is used during motor activation. In most devices described above that use a pressurized can or a liquid pump, a motor is coupled to the nozzle of the container through a gear and hammer arrangement. When the motor is activated, the nozzle of the container is depressed by the hammer resulting in dispensing of the odorizing material from the container. The motor is periodically activated for a predetermined period of time at predetermined intervals, causing a known power drain. It has been found that in these devices, the nozzle of the container is, at sometimes, depressed for a longer period of time than is necessary to activate dispensing. This is required to allow for a lower than optimal battery voltage level after some period of usage. In such systems, when the energy level of the battery is less than maximum, but still within operating parameters, nozzle depression occurs with less force and occurs more slowly, often resulting in dispensing of an inadequate amount of odorizing, disinfecting, or cleaning chemical. At very low battery levels, torque may be inadequate for the dispensing of any material.

To prevent this situation from occurring, the above-described devices are designed such that the motor causes the nozzle to be depressed for a predetermined period of time that is longer than necessary, such that a minimum amount of odorizing, cleaning, or disinfecting chemical will always be dispensed, even if the batteries are somewhat depleted. Accordingly, when the power level of the batteries is at a maximum, the motor continues to be energized even after the nozzle has been fully depressed and cannot be displaced any further. This is referred to as a motor stall condition because the motor is energized but the mechanical components cannot be further displaced, causing the motor to stop rotation.

Thus, during the dispensing cycle for known devices, especially when the batteries are at a full power level, the nozzle is fully depressed while the motor enters the stall condition. As described above, this guarantees that an adequate amount of odorizing, cleaning, or disinfecting chemical will be dispensed, even when the batteries are at a relatively low power level. Typically, the stall condition is terminated when a timer expires which deactivates the motor. However, applying power to the motor during a stall condition consumes a large portion of the stored power available from the batteries. The amount of power consumed during a motor stall condition is greater than the amount of power consumed during normal motor activation. This adversely affects the battery life and renders many of the above-described devices inadequate. To many consumers, the useful battery life of the dispensing device is the single most important factor in determining the acceptability and hence, the desirability of the device. Therefore, power efficiency is critical.

Additionally, a motor stall condition places excessive stress on the motor and on the gear arrangement used to convert motor motion into a nozzle-depressing motion. Excessive stress placed on the various mechanical components of the device may cause early component failure.

Accordingly, it is an object of the present invention to provide novel apparatus to substantially overcome the above-described problems.

It is another object of the present invention to provide a novel device for dispensing material that significantly reduces power consumption so that battery life is greatly increased.

It is a further object of the present invention to provide a novel device for dispensing material having a stall detection circuit to eliminate motor stall conditions.

It is also an object of the present invention to provide a novel device for dispensing material that eliminates motor stall conditions to greatly reduce the power drain on the batteries.

It is a further object of the present invention to provide a novel device for dispensing material having very low power requirements such that the batteries operating the dispensing device rarely need to be replaced.

SUMMARY OF THE INVENTION

The disadvantages of present dispensing devices are substantially overcome with the present invention by providing a novel apparatus for dispensing material, such as odorizing, cleaning, or disinfecting material, having extremely low power consumption requirements. The novel dispensing device is particularly energy efficient resulting in a substantial increase in battery life. According to a specific embodiment of the present invention, battery power is conserved by utilizing a novel motor stall detection circuit. The invention also eliminates the need to have an excessively long predetermined period of time during which the nozzle of the container is depressed.

The invention significantly reduces power consumption by detecting a motor stall condition and deactivating the motor as soon as the condition is detected. Accordingly, the nozzle of the container is depressed only through the maximum stroke of the motor and gear mechanism. As soon as the end of the full stroke is reached, the motor stall condition is detected and the motor is deactivated. A significant power savings is realized in this way.

More specifically, one embodiment of the invention comprises apparatus for dispensing material from a container having a dispensing element including a motor for repeatedly actuating the dispensing element to facilitate dispensing of the material from the container, and a controller for activating the motor at time intervals. The apparatus includes a stall detection circuit coupled to the motor and to the controller to detect a stall condition of the motor where the stall detection circuit is configured to issue a stall detection signal when the stall condition is detected. The controller deactivates the motor in response to receiving the stall detection signal.

According to another aspect of the invention, a specific embodiment of the invention includes a motor for repeatedly actuating a dispensing element to facilitate dispensing of the material from a container, batteries for providing electrical power to the motor, a gear mechanism coupled to the motor, and a hammer mechanism coupled between the gear mechanism and the dispensing element, where the gear mechanism is configured to convert mechanical motion of the motor into displacement of the hammer mechanism such that the hammer mechanism actuates the dispensing element. Also included is a controller for activating the motor at predetermined time intervals and a stall detection circuit coupled to the motor and to the controller to detect a stall condition of the motor, where the stall detection circuit is configured to issue a stall detection signal when the motor stall condition is detected. The controller deactivates the motor in response to receiving the stall detection signal.

BRIEF DESCRIPTION OF THE DRAWINGS

The features of the present invention which are believed to be novel are set forth with particularity in the appended claims. The invention, together with further objects and advantages thereof, may best be understood by reference to the following description in conjunction with the accompanying drawings.

DETAILED DESCRIPTION OF THE INVENTION

Figure 1A:
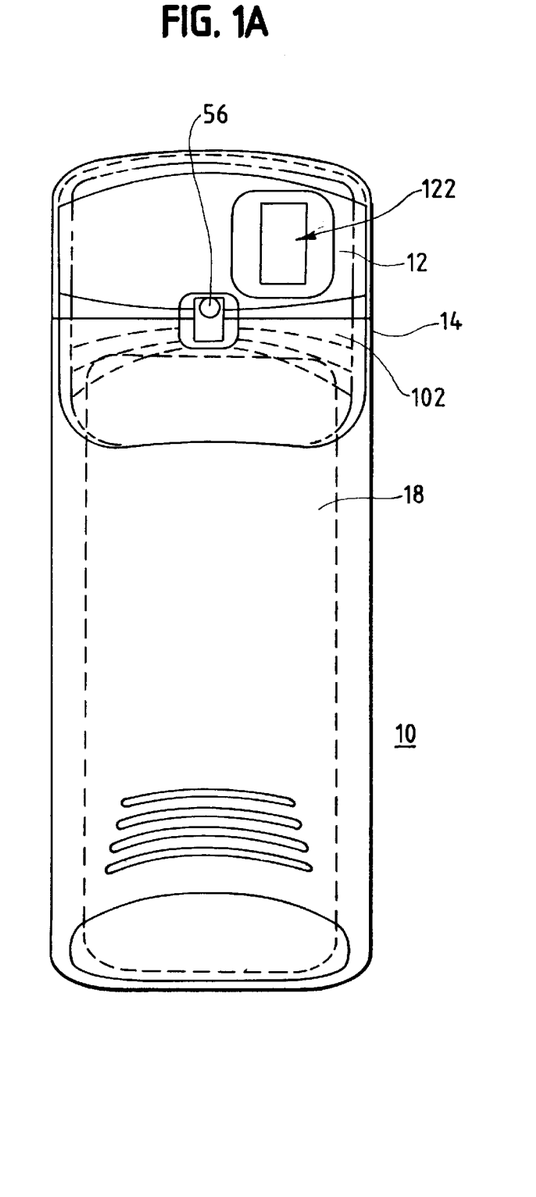
FIG. 1A is a front elevational view of a specific embodiment of a dispensing apparatus, according to the present invention.
Figure 1B:
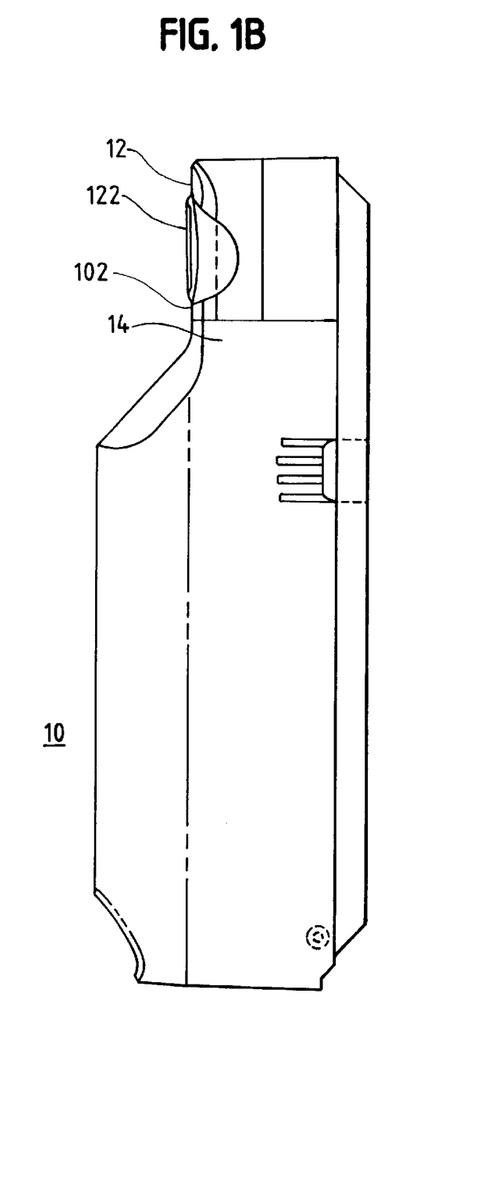
FIG. 1B is a side elevational view of the dispensing apparatus shown in FIG. 1A.

Referring now to FIG. 1A and FIG. 1B, the dispensing device 10 is generally shown. The dispensing device 10 includes a front panel 12 attached to an enclosure 14, or formed integrally with the enclosure. The enclosure 14 may be formed from plastic or other suitable material. A container 18, shown in phantom in FIG. 1A, is housed within the enclosure 14 and in one embodiment may contain an odorizing, cleaning, or disinfecting chemical. The container 18 may be a pressurized aerosol type container where depression of a nozzle 56 attached to the container 18 causes a predetermined amount of chemical to be dispensed. However, the container 18 may also be a liquid pump type container or any other container where depression of the nozzle 56 dispenses material. The nozzle 56 is actuated by a hammer and cam mechanism (not shown) which is coupled to a motor (not shown) through a gearing mechanism (not shown). The hammer and cam mechanism, the motor, the gearing mechanism, and the mechanics of the dispensing device 10 generally, are described in U.S. Pat. No. 5,038,972 issued on Aug. 13, 1991, entitled Metered Aerosol Fragrance Dispensing Mechanism, reissued on Feb. 7, 1995 as Re. U.S. Pat. No. 34,847, both of which are owned by the common assignee of this patent/patent application and are hereby incorporated by reference herein.

Figure 2:
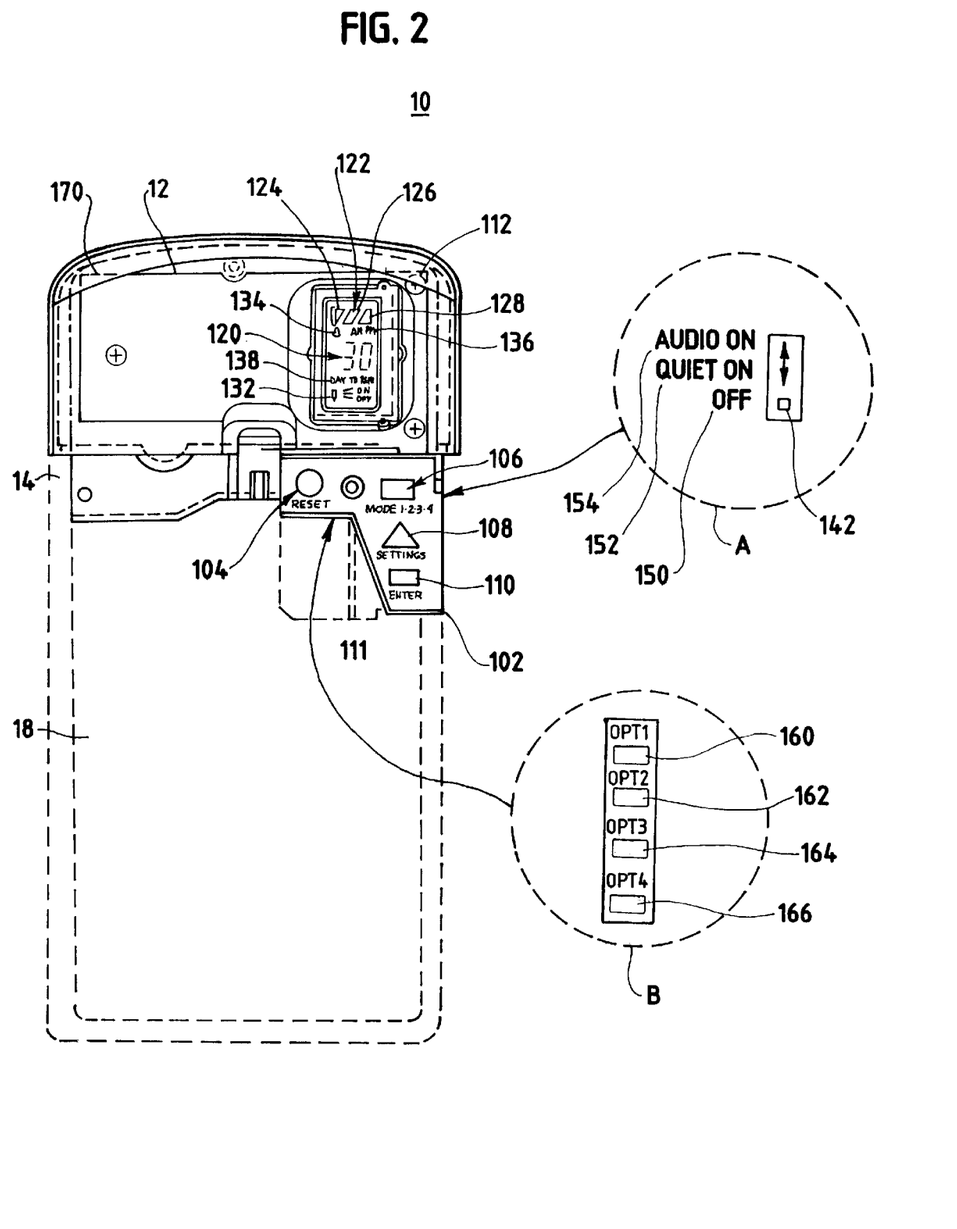
FIG. 2 is a pictorial representation of a portion of a front panel of one embodiment of the dispensing device shown in FIG. 1A, particularly illustrating control switches and an LCD display.

Referring now to FIG. 2, one embodiment of the invention is shown in which a control panel 102 is mounted on the front panel 12 or may be integrally formed with the front panel 12. The control panel 102 includes a reset switch 104, a mode switch 106, a "settings" or "adjust" switch 108, an enter switch 110, a manual on/off rocker-type switch 111, and a liquid crystal display (LCD display) 112 having several separate LCD portions. The reset switch 104, the mode switch 106, the settings switch 108, and the enter switch 110 are all pushbutton type momentary contact switches in the illustrated embodiment and may provide multiple functions when depressed multiple times in succession, as will be described in greater detail hereinafter. Of course, the switches described above may be any type of suitable button or switch known in the art.

Figure 3:
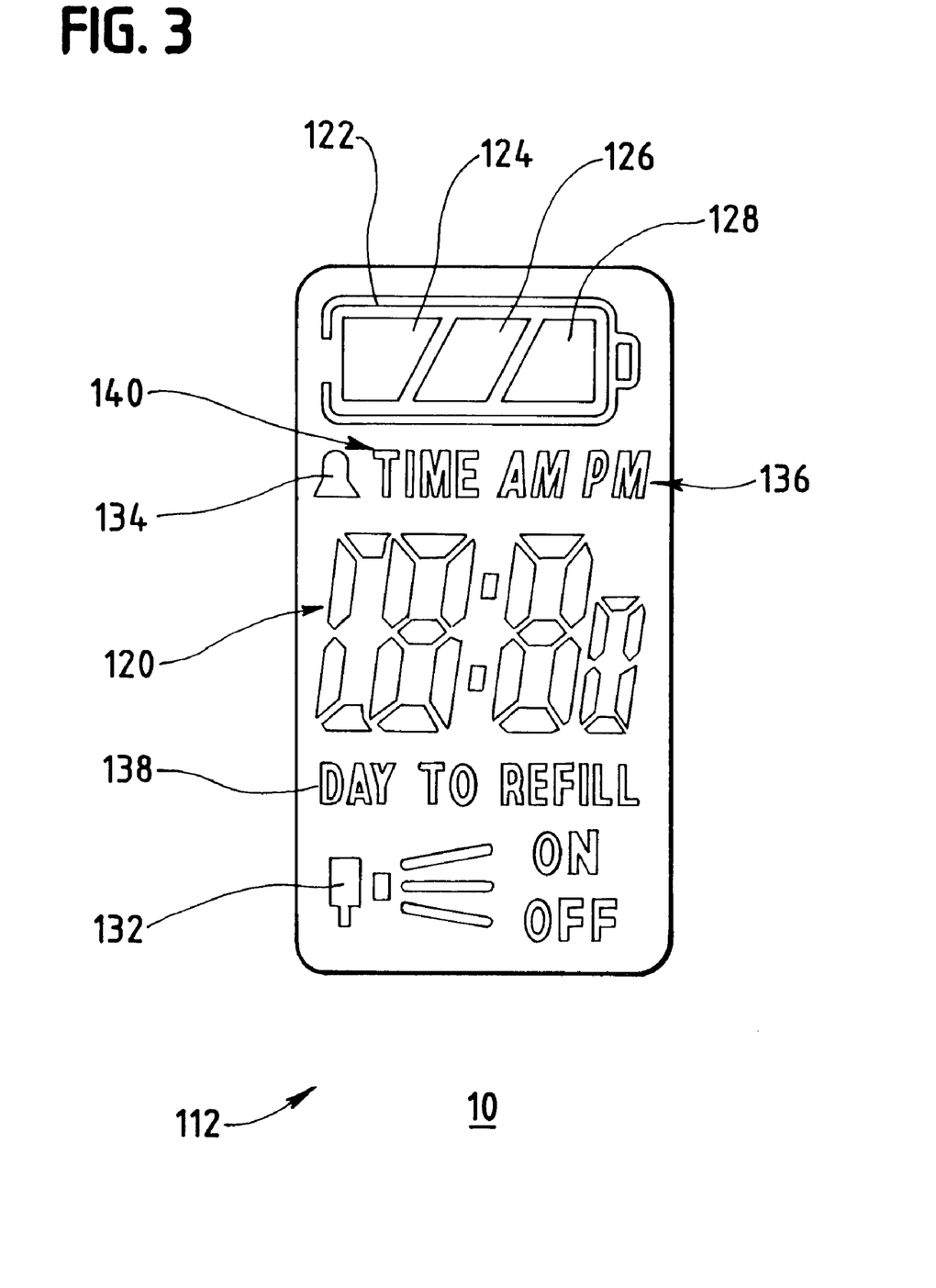
FIG. 3 is an enlarged view of the LCD display shown in FIG. 2.

Referring now to FIGS. 2 and 3, FIG. 3 illustrates a specific embodiment of the LCD display 112 in greater detail. The LCD display 112 is preferably a three by thirty-four segment LCD having a numerical display 120 and other graphical icons, as will be described hereinafter. The LCD display 112 includes a three segment LCD graphical display 122 that appears in the shape of a battery having three separate portions formed by a first segment 124, a second segment 126, and a third segment 128. The three segment graphical display 122 provides the user with an indication of remaining battery power. The LCD display 112 further includes graphical icons, such as a SPRAY (PUMP) on/off indicator 132 that indicates whether spray (pump) adjustments are currently being accessed, a tone icon 134 indicating that generation of audible tones or other audio indicators is enabled, an AM/PM indicator 136, a "DAYS TO REFILL" indicator 138, and a TIME indicator 140 for setting time (FIG. 3). The DAYS TO REFILL indicator 138, when enabled, indicates that the number represented by the numerical display 120 is the number of days left until the container 18 (FIG. 1) must be refilled or replaced.

A three-position slide switch 142 (FIG. 2) is provided under the control panel 102. The slide switch 142 is labeled as "A" in FIG. 2. The slide switch 142 controls the generation of tones, depending whether the switch is in an OFF position 150, a QUIET-ON position 152, or an AUDIO-ON position 154, as will be described in greater detail hereinafter.

A number of jumpers are provided on a printed circuit board (not shown) within the device for configuration of the product during manufacture, and are not intended to be accessed by the user. These jumpers may be removable or cuttable jumpers, or simply traces on the printed circuit board that can be abraded, severed, or cut as required. These jumpers, designated option 160, option 162, option 164, and option 166, are shown labeled as "B" in FIG. 2. Briefly, option 160 selects between a 0.7 second and a 0.9 second motor activation time, option 162 selects between a 0.1 second delay or no time delay for motor actuation, option 164 selects between a 3000 and a 6000 actuation cycle, and option 166 selects between an end-stop condition and a non-stop mode after a refill count has been reached. The function of the option switches or jumpers 160, 162, 164, and 166 will be described in greater detail hereinafter with reference to FIG. 4.

In operation, the dispensing device 10 of the illustrated embodiment functions as follows. Upon initial activation by turning on the device via on/off switch 170, or after the batteries have been installed or replaced, the reset switch 104 is briefly depressed. The reset switch 104 is a pushbutton type switch that cause the electronics of the dispensing device 10 to be reset. The reset switch 104 is also briefly depressed when the container 18 is replaced to permit recalculation of the time remaining until refill.

The above-described dispensing device 10 is not limited to dispensing material from a pressurized aerosol container 18. The dispensing device 10 may include, for example, a liquid pump container, a liquid drip container, or other suitable container. Further, the dispensing device may be adapted to dispense solid material.

Figure 4A:
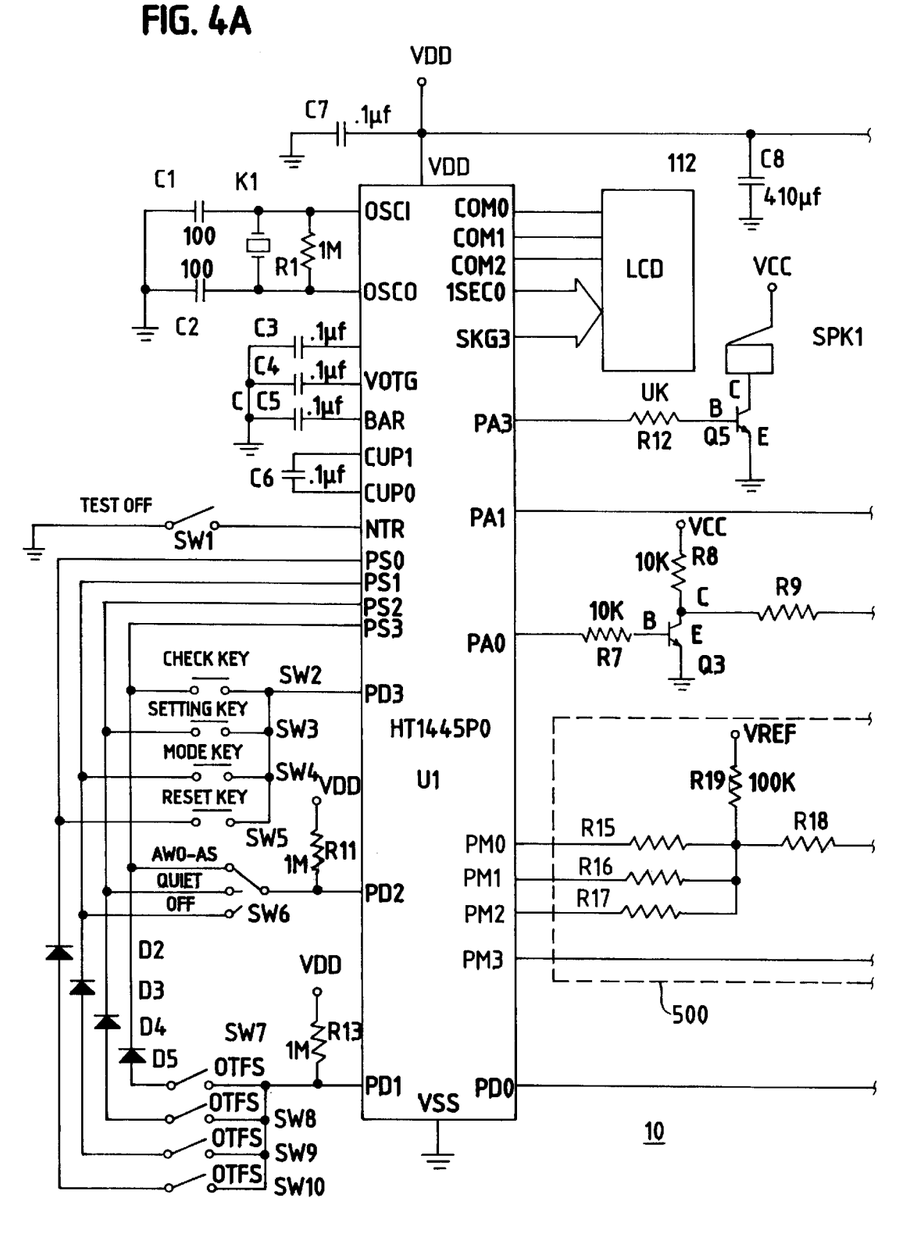
FIG. 4 is a schematic circuit diagram of a specific embodiment of control circuitry for the dispensing device of FIG. 1A.
Figure 4B:
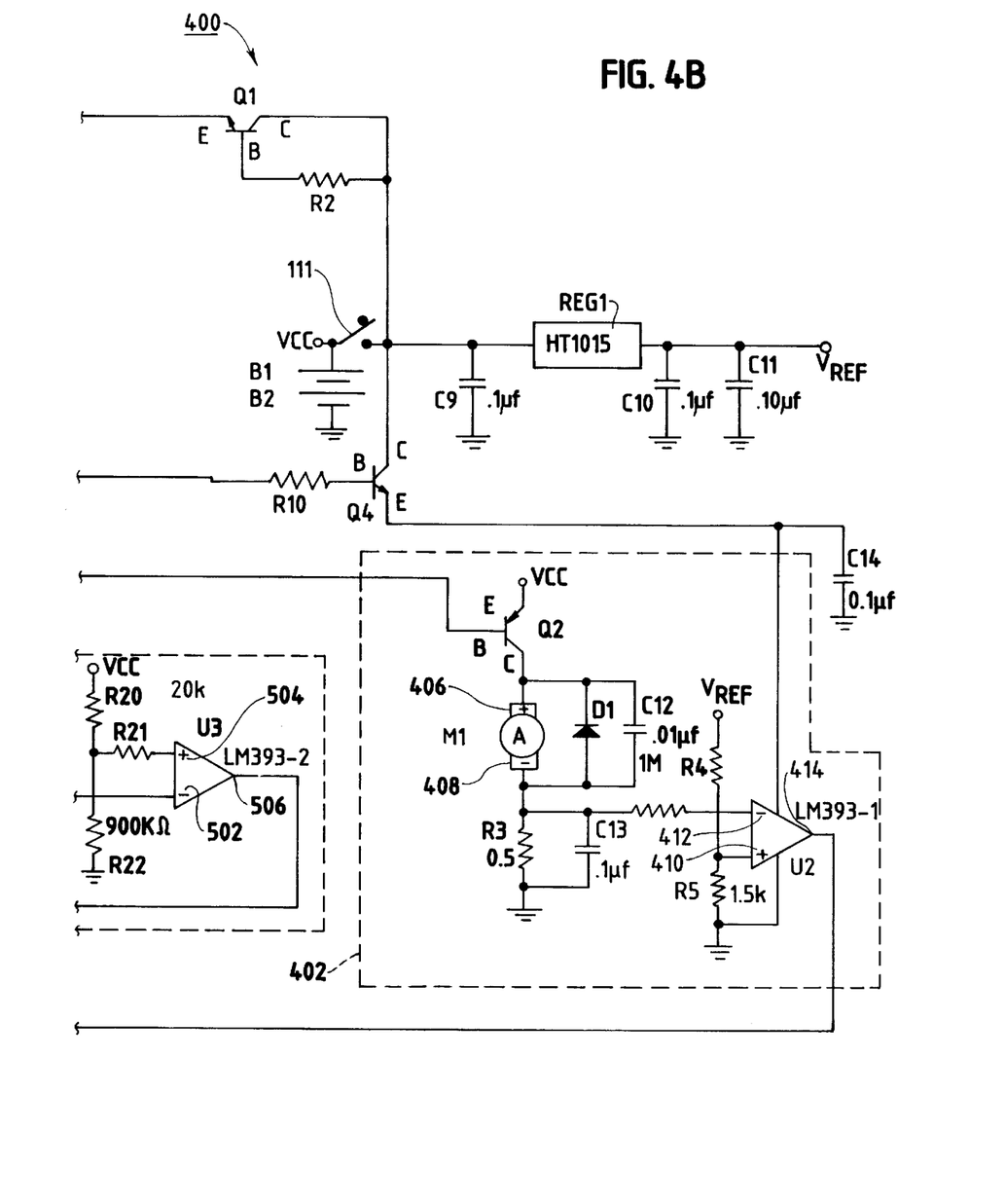

Referring now to FIG. 4, there is shown a schematic diagram for a specific embodiment of electronic circuitry for the illustrated embodiment of the dispensing device 10 (FIG. 1). Table 1 provides examples of component designations, component definition, and typical values or types, where applicable for a specific embodiment of the circuit of FIG. 4. Table 2 provides information about a specific microprocessor U1 for one embodiment for the circuit of FIG. 4 and includes a definition of the pad number, the pad name, input/output definition, mask option, and function of the microprocessor pin.

TABLE 1

| DESIGNATION | COMPONENT | VALUE/TYPE |
|---|---|---|
| B1, B2 | Battery | 1.5 volt |
| C1 | Capacitor | 100 pF |
| C2 | Capacitor | 100 pF |
| C3–C5 | Capacitor | 0.1 uF |
| C6 | Capacitor | 0.1 uF |
| C7 | Capacitor | 0.1 uF |
| C8 | Capacitor | 470 uF |
| C9–C10 | Capacitor | 0.1 uF |
| C11 | Capacitor | 10 uF |
| C12 | Capacitor | 0.01 uF |

TABLE 1-continued

| DESIGNATION | COMPONENT | VALUE/TYPE |
|---|---|---|
| C13 | Capacitor | 0.1 uF |
| C14 | Capacitor | 0.1 uF |
| D1 | Diode | 1N4148 or Equiv. |
| D2–D5 | Diode | 1N4148 or Equiv. |
| LCD | LCD 3 × 11 segment display | 3 × 11 segment |
| M1 | Motor | KF-510-18315 |
| Q1 | Transistor - NPN | 2SC945 or Equiv. |
| Q2 | Transistor - PNP | 2S3562 or Equiv. |
| Q3 | Transistor - NPN | 2SC945 or Equiv. |
| Q4 | Transistor - NPN | 2SC945 or Equiv. |
| Q5 | Transistor - NPN | 2SC945 or Equiv. |
| R1 | Resistor | 100 MΩ |
| R2 | Resistor | 1 KΩ |
| R3 | Resistor | 0.5 Ω |
| R4 | Resistor | 473 KΩ |
| R5 | Resistor | 15 KΩ |
| R6 | Resistor | 220 KΩ |
| R7 | Resistor | 10 KΩ |
| R8 | Resistor | 10 KΩ |
| R9 | Resistor | 75 Ω |
| R10 | Resistor | 13 KΩ |
| R11 | Resistor | 1 MΩ |
| R12 | Resistor | 1 KΩ |
| R13 | Resistor | 1 MΩ |
| R15 | Resistor | 105 KΩ |
| R16 | | 80.6 KΩ |
| R17 | | 63.4 KΩ |
| R18 | Resistor | 220 KΩ |
| R19 | Resistor | 10 KΩ |
| R20 | Resistor | 10 KΩ |
| R21 | Resistor | 530 KΩ |
| R22 | Resistor | 500 KΩ |
| REG1 | Voltage Regulator | HT1015 |
| SW1–SW5 | Momentary contact switch | Momentary contact switch |
| SW6 | Three position slide switch | DP3T |
| SW7–SW10 | Slide switch | SPST |
| U1 | Microprocessor | HT445P0 |
| U2–U3 | Operational amplifier | LM393 |
| X1 | Crystal | 32,760 kHz |

TABLE 2-MICROPROCESSOR U1

TABLE 2

| | | | MICROPROCESSOR U1 | |
|---|---|---|---|---|
| Pad No. | Pad Name | I/O | Mask Option | Function |
| 1, 34–65 | SEG33–SEG03 | O | — | LCD driver outputs for LCD segments |
| 2–5 6–9 10–13 | PS0–PS3 PD3–PD0 PM0–PM3 | I/O | CMOS, PMOS, NMOS, Wake-up Pull-high, Pull-low latch or none | 4-bit input/output port with tri-state register |
| 14 | RES/ | I | — | Input to reset an internal LSI Reset is active on a low level with an internal pull-high resistor |
| 15 | TEST/ | I | — | For test mode only the TEST pin should be left open for normal operation |
| 16 | INT/ | I | — | Input (with a pull-high resistor) for an external interrupt. Activated on a high to low edge trigger |

TABLE 2-continued

MICROPROCESSOR U1

| Pad No. | Pad Name | I/O | Mask Option | Function |
|---|---|---|---|---|
| 17 | $V_{SS}$ | I | — | transition<br>Negative power supply, GND |
| 18 | TMCLK | I | Internal frequency source and pull-high or none | Input for TIMER clock. TIMER can be clocked by an external clock or internal frequency source. |
| 19–22 | PA0–PA3 | O | CMOS OR PMOS open drain | 4-bit output port PA3 for a carrier output, or 4-bit output ports PA1 and PA0 for PFD output. |
| 26 | BAR | I | — | Voltage divider capacitor |
| 27 | $V_{DD}$ | I | — | Positive power supply |
| 28 | OSCI | I | Crystal or RC | OSCI and OSCO are connected to a resistor (RC) or a crystal for an internal system clock. |
| 29 | OSCO | O | | |
| 30–32 | COM0–COM2 | O | ½ or ⅓ duty | Outputs for LCD commons |
| 25 | VOTG | I | — | Voltage doubler capacitor |
| 33, 34 | CUP0, CUP1 | | | |

The schematic diagram of FIG. 4 in conjunction with Table 1 and Table 2 illustrate a circuit 400 that controls all of the functions of the dispensing device 10. The microprocessor U1 performs all control and display functions and operates the dispensing device 10 according to preprogrammed instructions. The microprocessor U1 may be, for example, a four-bit microcomputer model HT445P0 provided by Holtek, Inc. However, any suitable microcomputer or controller capable of controlling LCDs (liquid crystal display) and having input and output port capability may be used.

The microprocessor U1 includes a crystal X1 coupled between pads OSCI and OSCO. A resistor R1 is connected in parallel across the crystal X1 while capacitors C1 and C2 respectively, are coupled between each end of the crystal and ground. The crystal X1 may be, for example, a 32,760 kHz quartz crystal from which the microprocessor U1 derives its timing signals and clock signals.

Pads RES/, VOTG, and BAR are coupled to capacitors C3, C4, and C5, respectively, to ground. A capacitor C6 is also connected between pads CUP1 and CUP2 and functions as a voltage doubler capacitor, as is required for proper operation of the microprocessor U1. The circuit 400 receives electrical power from two 1.5 volt batteries B1 and B2. Electrical power supplied directly by the batteries B1 and B2 is labeled Vcc. The switch 111 selectively connects the batteries B1 and B2 to the circuit 400. The microprocessor U1 receives power on pad VDD which is coupled to the batteries B1 and B2 through transistor Q1. A resistor R2 is connected across the base and collector of the transistor Q1 to bias the transistor to conduct, thereby supplying the battery voltage Vcc, minus a small voltage drop, to pad VDD. A noise filtering capacitor C7 and a battery backup capacitor C8 are also coupled between pad VDD of the microprocessor U1 and ground. The transistor Q1 and the capacitor C8 form a battery backup circuit such that when the batteries B1 and B2 are temporarily removed, the capacitor C8 continues to supply power to the microprocessor U1 for approximately ten minutes. Accordingly, all of the user selected options and default settings are retained when the batteries are replaced. When the batteries B1 and B2 are removed, the transistor Q1 is turned off preventing reverse current flow from the capacitor C8 to the other components of the circuit 400. This permits the microprocessor U1 to preserve the state of all of its internal memory and registers for a period of at least ten minutes. Thus, the customer is not inconvenienced when the batteries B1 and B2 are replaced since the microprocessor U1 "remembers" important data, such as the amount of odorizing chemical remaining in the container 18 (FIG. 1) and the number of days remaining until the container must be replaced.

The battery voltage Vcc is further connected to a voltage regulator device REG1 which provides a regulated voltage output labeled Vref. A noise filtering capacitor C9 is coupled between the input of voltage regulator REG1 and ground, while noise filtering capacitors C10 and C11 are coupled between the output of the voltage regulator REG1 and ground. The voltage regulator REG1 may be, for example, a Holtek, Inc. HT1015 voltage regulator which provides a fixed regulated output voltage. However, any suitable voltage regulator or zener diode may be used to provide a similar function.

A motor driver and stall detection circuit 402 is shown in dashed lines and includes a transistor Q2, a motor M1, a diode D1, capacitors C12 and C13, resistors R3, R4, R5, and R6, and a comparator U2. The comparator U2 may be, for example, one-half of an LM393 operational amplifier configured as a comparator. The motor M1 receives power from Vcc through the transistor Q2, which is switchably controlled by the microprocessor U1. An output bit PA0 of the microprocessor U1 is coupled to the base of a transistor Q3 via a resistor R7 while the collector of the transistor Q3 is coupled to Vcc through a pull-up resistor R8. The emitter of the transistor Q3 is connected to ground. The collector of the transistor Q3 is, in turn, coupled via a resistor R9 to the base of the transistor Q2. In operation, to activate the motor M1, the microprocessor U1, under software control, asserts a high level signal on the output bit PA0 causing the transistor Q3 to conduct. This forces the collector of the transistor Q3 to a low voltage level, which in turn, causes the transistor Q2 to conduct, thereby coupling the motor M1 between Vcc and ground, thus activating the motor. Of course, the motor M1 is supplied with the voltage level Vcc minus a small voltage drop caused by transistor Q2.

The comparator U2 also receives power Vcc through a switched transistor Q4 under microprocessor U1 control. An output bit PA1 of the microprocessor U1 is coupled to the base of the transistor Q4 via a resistor R10. The collector of the transistor Q4 is connected to Vcc while the emitter of the transistor Q4 is connected to the power pin of the comparator U2, and to a noise filtering capacitor C14. Thus, when the microprocessor U1 asserts a high level signal on the output bit PA1, the transistor Q4 conducts thereby supplying the voltage Vcc to the comparator U2. In this way, power to the comparator U2 can be disconnected during the time that the motor M1 is not activated to further conserve battery power. The comparator U2 function is only required during operation of the motor M1, as will be described in detail hereinafter. According, every effort is made to conserve battery power and to disconnect power from all components when not in use. Conservation of battery power is a significant feature of the novel device for dispensing odorizing material. Accordingly, all functions that use power have been selectively turned off when not in use. This includes disconnecting power from all components whose function is not currently needed, utilizing energy-efficient LCD displays, and minimizing power usage by the motor, as will be described hereinafter.

In an alternate embodiment, a solar cell and charging circuit is added to supply power to the battery to prolong the life of the battery. Accordingly, if sufficient light is supplied to the solar cell, the batteries may not need replacement.

Referring now to the motor driver and stall detection circuit 402, the diode D1 and the capacitor C12 are connected in parallel across a positive terminal 406 and a negative terminal 408 of the motor M1. This reduces the back-EMF which may be generated when the motor is de-energized. The motor M1 is connected between the source of power Vcc via the collector of the transistor Q2.

The non-inverting input 410 of the comparator U2 is coupled to the junction of the resistors R4 and R5. The resistors R4 and R5 form a voltage divider network that determines a threshold voltage level for the comparator U2. Note that the voltage reference supplied to the voltage divider combination of the resistors R4 and R5 is connected to the voltage source Vref, not to the voltage source Vcc. This is done so that a precise reference voltage may be maintained regardless of the voltage level of the batteries B1 and B2, assuming that the voltage level of the batteries is above the minimum operating voltage input level of the voltage regulator REG1.

The inverting input 412 of the comparator U2 is the signal input and is coupled to the negative terminal 408 of the motor M1 through the resistor R6. The common junction between the negative terminal 408 of the motor M1 and the end of the resistor R6 is coupled to the parallel combination of the resistor R3 and the capacitor C13. The other end of the parallel combination of the resistor R3 and the capacitor C13 is connected to ground. The output 414 of the comparator U2 is coupled to an input bit PD0 of the microprocessor U1 so that the microprocessor can determine the state of the comparator.

In operation, the motor driver and stall detection circuit 402 functions as follows. When the motor M1 is energized, current flows through the windings of the motor to ground. Because the resistor R3 is connected between the motor and ground, the motor current also flows through the resistor R3. The flow of current through the resistor R3 causes a voltage drop across the resistor. This voltage drop is routed to the inverting input 412 of the comparator U2 as the signal input to the comparator U2. Thus, the current flowing through the motor M1 is converted to a voltage and compared to the reference threshold voltage present at the non-inverting input 410 of the comparator U2. When the voltage level present at the inverting input 412 is less than the reference voltage present at the non-inverting input 5410, the output 414 of the comparator U2 is at a high voltage (logic level one), indicating that the current passing through the motor M1 is lower than a maximum defined level. This indicates normal operation of the motor M1. Conversely, when the voltage level present at the inverting input 412 is greater than the reference voltage present at the non-inverting input 410, the output 414 of the comparator U2 is at a low voltage (logic level zero), indicating that the current through the motor M1 is greater than a maximum allowed level. This indicates a motor stall condition. Such an indication of excessive current draw by the motor M1 is critical to conserving battery power because it permits the microprocessor U1 to correct the motor stall condition.

As described above, a motor stall condition occurs when the nozzle 56 (FIG. 1) of the container 18 (FIG. 1), such as an aerosol container or liquid pump container, is in a fully depressed state while the motor M1 continues to be energized. Known dispensing devices are intentionally configured to cause a motor stall condition sustained for a short period of time to guarantee that the nozzle 56 of the container 18 will be depressed for a sufficient period of time, particularly when the batteries are at a low power level. However, in the present novel invention, no such energy consuming stall is needed because the proper amount of material is dispensed without sacrificing battery power by immediately detecting and eliminating a motor stall condition.

It has been determined that an excessive amount of battery power is consumed during a motor stall condition. During a motor stall condition, the motor M1 uses about two or more times the amount of current that is used during normal operation of the motor. Therefore, the present novel invention detects a motor stall condition and immediately deactivates the motor M1 to permit the nozzle 56 (FIG. 1) to return to its non-engaged position. Motor stall detection is based upon the detection of excessive current draw through the windings of the motor M1. This is performed by the comparator U2 which detects when a voltage level proportional to the current drawn by the motor M1 is greater than the threshold voltage Vref set by the voltage divider combination of R4 and R5. For example, in the illustrated embodiment of FIG. 4, the threshold voltage present at the non-inverting input 410 of the comparator U2 is equal to $(R5/(R4+R5))*Vref=0.0307 Vref$. Once the threshold voltage is exceeded by the signal present on the inverting input 412 of the comparator U2, the output 414 of the comparator becomes low and the microprocessor U2 detects this condition on the input bit PD0. The microprocessor U1 then deactivates the motor M1. This significantly reduces power drain on the batteries B1 and B2 by 60% to 70%, resulting in a highly significant power savings and extended battery life.

Detection and correction of the motor stall condition provides several significant advantages. In addition to a large reduction in energy consumption, detection of the motor stall condition and immediate deactivation of the motor M1 reduces stress on the housing 14 (FIG. 1) and the gearing mechanism (not shown). It has also been found that elimination of the motor stall condition reduces stress on the motor M1 by about 60%. Physical stress on the mechanical components during a motor stall condition is about three to four times the stress existing during a normal stroke or cycle. A stroke or cycle is defined to be one complete dispensing cycle where the motor causes the nozzle 56 (FIG. 1) of the container 18 (FIG. 1) to be fully depressed and subsequently released. Such increased stress on the components may crack or otherwise damage the housing 14 (FIG. 1) and gears. Detection and immediate elimination of the motor stall condition results in increased reliability and fewer component failures.

Additionally, due to operation based on detection of the motor stall condition, large variations in the components of the dispensing device 10 need not be taken into account during manufacturing because the required amount of material is dispensed during each cycle regardless of the tolerances and variations in the components, such as the gears and the motor M1. This is true because the present novel device does not function on a strictly timed basis. That is, to achieve proper dispensing of material from the container 18 (FIG. 1), the nozzle need not be depressed for a predetermined excessive period of time and with maximum force, as is done in known systems. Rather, the nozzle 56 (FIG. 1)

need only be depressed until a stall condition is detected and such depression is performed without regard to the power level of the batteries, assuming that the power level is above the absolute minimum required level. In other words, the motor M1 is activated for only the period of time required to complete one stroke of the hammer and cam mechanism (not shown). This is very different from known systems where the motor must be operated for a predetermined period of time to guarantee proper depression of the nozzle and subsequent release of odorizing material at various battery power operating levels. Thus, component variations affecting the duration of the cycle, the speed of the motor M1, the current draw and torque of the motor, gear tolerances, and other mechanical tolerances, may be essentially disregarded.

As described above, known dispensing devices energize the motor for a specific minimum period of time to ensure proper depression of the nozzle regardless of the level of remaining battery power, assuming that the power level is above the absolute minimum required level. This necessarily means that when the battery power levels are high, such as when the batteries are new, the motor is energized for an unnecessarily long period of time because the motor causes relatively rapid depression of the nozzle. This wastes a significant amount of power. The present novel dispensing device 10 dispenses the proper amount of odorizing, cleaning, or disinfecting material regardless of the power level of the batteries B1 and B2, assuming a power level greater than or equal to the minimum required level, because a single stroke of the hammer (not shown) is completed without regard to the speed or torque of the motor M1. The hammer (not shown) is engaged until the nozzle 56 (FIG. 1) is fully depressed, at which time the motor stall condition is detected and the microprocessor U1 deactivates the motor M1.

Figure 5:
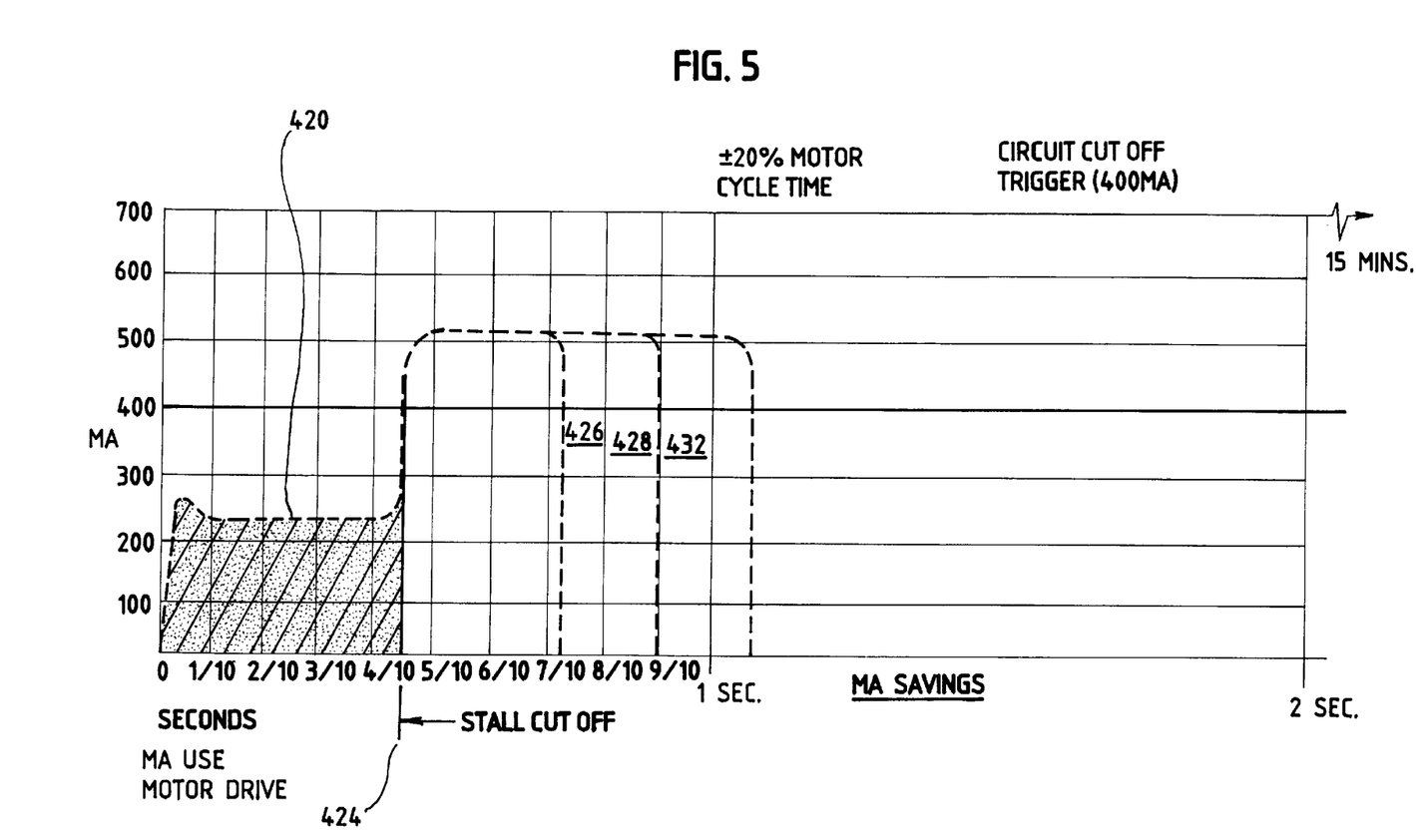
FIG. 5 is a graph depicting current consumption over time, particularly illustrating a motor stall condition.

Referring now to FIGS. 4 and 5, FIG. 5 graphically illustrates the motor stall condition according to a specific embodiment of the present invention. The motor stall condition causes a sharp increase in the current drawn by the motor M1 and appears in the form of a current "spike". As shown in FIG. 5, current is displayed in milliamperes on the "Y" axis while time is displayed in seconds on the "X" axis. The segment labeled 420 indicates usage of the motor M1 during normal operation or during a non-stall condition. The small increase in current shown by reference number 422 indicates current drawn during initial turn-on of the motor M1 and quickly comes to a steady state condition. In this specific example, by about 0.45 seconds into the cycle, a motor stall condition is entered, as indicated at segment 424. Once the motor stall condition is detected (by detection of the trigger threshold of 400ma as illustrated), the motor M1 is immediately deactivated. Segments 426, 428 and 430 illustrate the current consumption of known devices that do not correct the motor stall condition, but rather, de-energize the motor M1 at approx. 0.7 seconds, 0.9 seconds and 1.0 second, respectively, based strictly on a predetermined period of motor-activation time.

Referring now to FIGS. 2 and 4, microprocessor pad INTR/ is coupled to a momentary contact switch SW1. Depression of the switch SW1 causes the microprocessor U1 to enter a test mode and perform internal tests to check the integrity of internal components, such as RAM and ROM, input/output ports, and various registers (not shown). Four momentary contact switches SW2, SW3, SW4, and SW5 are connected to the microprocessor U1 input bit PS3 and to the cathode of diodes D2, D3, D4, and D5, respectively. The cathode of the diodes D2, D3, D4, and D5 are further coupled to microprocessor input bits PS3, PS2, PS1, and PS0 respectively. The switches SW2, SW3, SW4, and SW5 directly correspond to the enter switch 110, the settings switch 108, the mode switch 106, and the reset switch 104, respectively, shown in FIG. 2.

Referring now to FIG. 4, a three position slidable switch SW6 is coupled to microprocessor input bit PD, which is further pulled up to voltage $V_{DD}$ via a resistor R11 to provide a user-selectable tone option. The switch SW6 directly corresponds to the slidable switch 14 shown in FIG. 2 and provides the audio options of AUDIO-ON 154, QUIET-ON 152, and OFF 154, as shown in FIG. 2. An audio tone output is provided by an audio element SPK1, which may, for example, be a miniature speaker or a piezo-electric transducer. The audio element SPK1 is driven by the collector of a transistor Q5 that is controlled by the microprocessor U1 output bit PA3 coupled to the base of the transistor 05 via a current limiting resistor R12. Note that the tone icon 134 (FIGS. 2 and 3) is turned on only when the switch SW6 is set in the AUDIO-ON tone position to enable generation of the audible tone. When the switch SW6 is set in the OFF or the QUIET-ON position, the tone icon 134 is turned off.

Four toggle switches SW7–SW10 provide user options OPT1–OPT4, respectively. The four switches SW7–SW10 directly correspond to the switches or jumpers of FIG. 2 labeled option 160, option 162, option 164, and option 166. Each switch SW7–SW10 is coupled to an input bit PD1 of the microprocessor U1 and is pulled up to voltage $V_{DD}$ by a pull-up resistor R13. The other end of each switch SW7–SW10 is further coupled to the anode of the diodes D2, D3, D4, and D5, respectively. The switch SW7 controls selection of option OPT1. This permits the motor activation time to be either 0.7 or 0.9 seconds in duration. Variation of this parameter permits use of different gearing mechanisms associated with various models of the dispensing device 10, some of which may not implement the stall detection circuit. When the switch SW7 is open, a fixed motor activation time of 0.7 seconds is selected. When the 0.7 second duration option is selected, the motor stall detection circuitry is disabled. When the switch SW7 is closed, a fixed motor activation time of 0.9 seconds is selected.

As described briefly above, the options described are not normally selectable by a user. Option selection is made at the time of manufacture to satisfy particular product requirements.

The switch SW8 controls selection of option OPT2. This option is only selectable if the 0.9 second option of OPT1 has been selected. When the switch SW8 is open, a 0.1 second delay will elapse prior to declaring a motor stall condition. This option may be used because a small current spike occurs when the motor M1 is initially energized, as shown by reference numeral 422 of FIG. 5. To avoid erroneous detection of a motor stall condition when the "turn-on" spike occurs, the 0.1 second delay is introduced. When the switch SW8 is closed, no delay is introduced and the motor stall condition is immediately detected and reported when it occurs. The 0.1 second delay is also useful in insuring that pump compression in the pump-to-stall stroke is fully relieved.

The switch SW9 controls selection of option OPT3. When the switch SW9 is open, the dispensing device 10 indicates that the container 18 (FIG. 1) requires refilling after 3000 pump cycles. When the switch SW9 is closed, the dispensing device 10 indicates that the container 18 requires refilling after 6000 cycles or pump cycles. Selection of this option depends upon the volume of the container 18.

The switch SW10 controls selection of option OPT4. When the switch SW10 is open, the dispensing device 10 stops when the maximum count of number of cycles has been reached, depending whether 3,000 or 6,000 cycles has been set by option OPT3. The user may be informed that the container 18 (FIG. 1) requires replacement by audible and visual means, as will be described in greater detail hereinafter. When the switch SW10 is closed, the dispensing device 10 does not stop when the maximum count of number of cycles has been reached. Instead, a dispensing operation still occurs at the appropriate time, but the counter no longer counts dispensing cycles. This option is useful in situations where the bottle 18 may not be completely empty due to pumping tolerances and the degree to which the bottle was filled at installation.

Specific embodiments of an apparatus for dispensing material according to the present invention have been described for the purpose of illustrating the manner in which the invention may be made and used. It should be understood that implementation of other variations and modifications of the invention and its various aspects will be apparent to those skilled in the art, and that the invention is not limited by the specific embodiments described. It is therefore contemplated to cover by the present invention any and all modifications, variations, or equivalents that fall within the true spirit and scope of the basic underlying principles disclosed and claimed herein.

What is claimed is:

1. An apparatus for dispensing material having a dispensing element, the apparatus comprising:
   a motor for repeatedly actuating the dispensing element to facilitate dispensing of the material;
   a stall detector coupled to the motor to detect a stall condition of the motor, the stall detector configured to issue a stall detection signal when the stall condition is detected; and
   a controller configured to activate the motor at time intervals and to deactivate the motor in response to the stall detection signal.

2. The apparatus according to claim 1 wherein the stall detector circuit is configured to detect a current spike associated with the motor when the motor enters a stall condition.

3. The apparatus according to claim 1 wherein the stall detector includes a resistive element coupled to the motor, the resistive element developing a voltage there across proportional to a current flowing through the motor.

4. The apparatus according to claim 3 wherein the stall detector includes a comparator that compares the voltage developed across the resistive element with a reference voltage, and issues the stall detection signal if the voltage developed is not within a predetermined voltage relative to the reference voltage.

5. The apparatus according to claim 3 wherein the voltage developed across the resistive element is developed in response to current drawn by the motor when the motor enters a stall condition.

6. The apparatus according to claim 3 wherein power to at least some circuitry in addition to the motor is deactivated as a result of issuance of the stall detection signal during at least a portion of periods when the motor is deactivated.

7. The apparatus according to claim 1 further including at least one battery for providing electrical power to the motor.

8. The apparatus according to claim 7 wherein deactivation of the motor in response to receiving the stall detection signal also results in deactivation of at least a portion of the stall detector to reduce power drain on the batteries such that battery life is extended.

9. The apparatus according to claim 7 further including solar power means configured to charge the batteries.

10. The apparatus according to claim 1 wherein the dispensing element is at least one of a nozzle and a stem element, corresponding to at least one of a pressurized aerosol container and a liquid pump container.

11. An apparatus for dispensing material from a container having a dispensing element, the apparatus comprising:
    a motor for repeatedly actuating the dispensing element to facilitate dispensing of the material from the container;
    stall detection means coupled to the motor for detecting a stall condition of the motor, the stall detection means configured to detect a sharp rise in current used by the motor when the motor enters a stall condition, detection of the rise in current causing issuance of a stall detection signal;
    a switchable power source coupled to the motor for activating and deactivating the motor, the switchable power source configured to deactivate the motor upon generation of the stall detection signal.

12. The apparatus according to claim 11 wherein the stall detection means includes a resistive element coupled to the motor such that a voltage developed across the resistive element is proportional to a current flow through the motor.

13. The apparatus according to claim 12 wherein the stall detection means includes a means for determining whether the voltage developed across the resistive element is within a predetermined voltage relative to a reference voltage.

14. The apparatus according to claim 11 wherein the stall detection means is configured to detect a current spike associated with the motor when the motor enters a stall condition.

15. The apparatus according to claim 12 wherein the stall detection means includes a comparator that compares the voltage developed across the resistive element with a reference voltage, and issues the stall detection signal if the voltage developed is not within a predetermined voltage relative to the reference voltage.

16. The apparatus according to claim 11 further including at least one battery for providing electrical power to the motor.

17. The apparatus according to claim 16 wherein deactivation of the motor in response to receiving the stall detection signal reduces a power drain on the batteries such that battery life is extended.

18. The apparatus according to claim 12 wherein the resistive element is coupled in series with the motor such that the voltage developed across the resistive element is proportional to the current flowing through the motor.

19. The apparatus according to claim 11 wherein the switchable power source includes a switchable element responsive to the stall signal.

20. The apparatus according to claim 19 wherein the switchable element is a semiconductor switch.

21. An apparatus for dispensing material from a container having a dispensing element, the apparatus comprising:
    a motor for repeatedly actuating the dispensing element to facilitate dispensing of the material from the container;
    at least one battery for providing electrical power to the motor;
    a gear mechanism coupled to the motor;
    a hammer mechanism coupled between the gear mechanism and the dispensing element, the gear mechanism configured to displace the hammer mechanism such that the hammer mechanism actuates the dispensing element;

a stall detection circuit coupled to the motor to detect a stall condition of the motor, the stall detection circuit configured to issue a stall detection signal when the stall condition is detected; and a controller which activates the motor at time intervals and deactivates the motor in response to the stall detection signal.

22. Method for dispensing material comprising the steps of:

a) activating an electric motor to actuate a dispensing cycle to dispense a desired amount of the material;

b) detecting a stall condition of the motor;

c) deactivating the motor in response to detection of the stall condition.

23. The method of claim 22 wherein detecting a stall condition comprises detecting a current spike associated with the motor when the motor enters a stall condition.

24. The method of claim 22 further comprising deactivating other circuitry in addition to the motor in response to detection of the stall condition.

* * * * *